US012611379B2

(12) United States Patent
Gao et al.

(10) Patent No.: US 12,611,379 B2
(45) Date of Patent: Apr. 28, 2026

(54) LIPID NANO DRUG DELIVERY SYSTEM TARGETING BRAIN LESION AND PREPARATION METHOD AND APPLICATION THEREOF

(71) Applicants: SHANGHAI JIAOTONG UNIVERSITY SCHOOL OF MEDICINE, Shanghai (CN); SHANGHAI SECOND MEDICAL INVESTMENT MANAGEMENT CO. LTD, Shanghai (CN)

(72) Inventors: Xiaoling Gao, Shanghai (CN); Qingxiang Song, Shanghai (CN); Gan Jiang, Shanghai (CN); Lepei Chen, Shanghai (CN)

(73) Assignees: SHANGHAI JIAOTONG UNIVERSITY SCHOOL OF MEDICINE, Shanghai (CN); SHANGHAI SECOND MEDICAL INVESTMENT MANAGEMENT CO. LTD, Shanghai (CN)

( * ) Notice: Subject to any disclaimer, the term of this patent is extended or adjusted under 35 U.S.C. 154(b) by 994 days.

(21) Appl. No.: 17/776,217

(22) PCT Filed: Nov. 13, 2020

(86) PCT No.: PCT/CN2020/128748
§ 371 (c)(1),
(2) Date: May 11, 2022

(87) PCT Pub. No.: WO2021/098606
PCT Pub. Date: May 27, 2021

(65) Prior Publication Data
US 2022/0401362 A1 Dec. 22, 2022

(30) Foreign Application Priority Data
Nov. 22, 2019 (CN) ......................... 201911157549.0

(51) Int. Cl.
*A61K 9/00* (2006.01)
*A61K 47/64* (2017.01)
*A61P 25/00* (2006.01)

(52) U.S. Cl.
CPC .......... *A61K 9/0085* (2013.01); *A61K 47/645* (2017.08); *A61P 25/00* (2018.01)

(58) Field of Classification Search
None
See application file for complete search history.

(56) References Cited

FOREIGN PATENT DOCUMENTS

| CN | 102525935 A | 7/2012 |
| CN | 104138600 A | 11/2014 |
| CN | 108451929 A | 8/2018 |
| CN | 110124018 A | 8/2019 |
| WO | 2015017034 A1 | 2/2015 |

OTHER PUBLICATIONS

Chen et al. "Tailored Reconstituted Lipoprotein for Site-Specific and Mitochondria-Targeted Cyclosporine A Delivery to Treat Traumatic Brain Injury" ACS Nano 14:6636-6648. (Year: 2020).*
Nov. 14, 2023 Japanese Second Office Action issued in Japanese application No. 2022-529787.
Jul. 17, 2023 English Office Action issued in EP Patent Application No. 20890093.6.
Jun. 20, 2023 Japanese Office Action issued in JP Patent Application No. 2022-529787.
Zhang Si et al: "Distinct roles for metalloproteinases during traumatic brain injury" Neurochemistry international, vol. 96, Jun. 1, 2016 (Jun. 1, 2016) , pp. 46-55, XP093060956, Amsterdam, NL.
Jan. 29, 2021 International Search Report issued in International Patent Application No. PCT/CN2020/128748.
Jan. 29, 2021 Written Opinion of the International Searching Authority issued in International Patent Application No. PCT/CN2020/128748.
Chen, L. P. et al. "Tailored Reconstituted Lipoprotein for Site-Specific and Mitochondria Targeted Cyclosporine A Delivery to Treat Traumatic Brain Injury" ACS Nano, vol. 14. May 28, 2020 (May 28, 2020) pp. 6636-6648.
Huang, M. et al. "GM1-Modified Lipoprotein-like Nanoparticle: Multifunctional Nanoplatform for the Combination Therapy of Alzheimer's Disease" ACS Nano, vol. 9, No. 11, Oct. 6, 2015 (Oct. 6, 2015), pp. 10801-10816.

(Continued)

*Primary Examiner* — Sudhakar Katakam
*Assistant Examiner* — Zachary J Miknis
(74) *Attorney, Agent, or Firm* — Houston Beshining Law Office PLLC; Liangang Ye

(57) ABSTRACT

A lipid nano drug delivery system targeting a brain lesion and a preparation method and application thereof. The drug delivery system comprises a lipid, a delivery drug, and a functional penetrating peptide, and the functional penetrating peptide is formed by covalently connecting a peptide chain linking a nanocarrier end, an arginine-rich penetrating peptide, a matrix metalloproteinase-9 sensitive peptide, and a polyanion inhibitory peptide. The lipid nano drug delivery system can be used for targeting the brain lesion and realizing mitochondrial enrichment by means of modification of the functional penetrating peptide. The repair of mitochondria is realized by encapsulating peptide drug cyclosporin A by means of a lipid nanoparticle core by utilizing a dilution-induced precipitation technique, thereby solving the problems that current cyclosporin A is difficult to effectively reach a brain lesion and the therapeutic window is small, and improving the ability to repair cells around the brain lesion with a small administration dose.

15 Claims, 5 Drawing Sheets

Specification includes a Sequence Listing.

(56)                    References Cited

OTHER PUBLICATIONS

Gao, W. et al. Chemotherapeutic drug delivery to cancer cells using a combination of folate targeting and tumor microenvironment-sensitive polypeptides Biomaterials, vol. 34. Mar. 1, 2013 (Mar. 1, 2013) pp. 4137-4149.

Lamade, A.M. et al. "Aiming for the Target:Mitochondrial Drug Delivery in Traumatic Brain Injury" Neuropharmacology, vol. 145, Feb. 28, 2019 (Feb. 28, 2019) pp. 209-219.

Chinese priority application No. 201911157549.0 (not published).

May 27, 2025 First Office Action issued in European Patent Application No. 20890093.6.

* cited by examiner

SEQUENCE LISTING

```
<160> NUMBER OF SEQ ID NOS: 23

<210> SEQ ID NO 1
<211> LENGTH: 45
<212> TYPE: PRT
<213> ORGANISM: Artificial Sequence
<220> FEATURE:
<223> OTHER INFORMATION: functional penetrating peptide
<220> FEATURE:
<221> NAME/KEY: BINDING
<222> LOCATION: (1)..(1)
<223> OTHER INFORMATION: Ac-

<400> SEQUENCE: 1

Phe Ala Glu Lys Phe Lys Glu Ala Val Lys Asp Tyr Phe Ala Lys Phe
1               5                   10                  15

Trp Asp Gly Ser Gly Arg Arg Arg Arg Arg Arg Arg Arg Pro Val
            20                  25                  30

Gly Leu Ile Gly Glu Gly Gly Glu Gly Gly Glu Gly Gly
        35                  40                  45

<210> SEQ ID NO 2
<211> LENGTH: 46
<212> TYPE: PRT
<213> ORGANISM: Artificial Sequence
<220> FEATURE:
<223> OTHER INFORMATION: functional penetrating peptide
<220> FEATURE:
<221> NAME/KEY: BINDING
<222> LOCATION: (1)..(1)
<223> OTHER INFORMATION: Ac-

<400> SEQUENCE: 2

Phe Ala Glu Lys Phe Lys Glu Ala Val Lys Asp Tyr Phe Ala Lys Phe
```

```
1               5              10             15

Trp Asp Gly Ala Gly Ala Arg Arg Arg Arg Arg Arg Arg Arg Pro
            20              25              30

Val Gly Leu Ile Gly Glu Gly Gly Glu Gly Gly Glu Gly Gly
        35              40              45

<210> SEQ ID NO 3
<211> LENGTH: 44
<212> TYPE: PRT
<213> ORGANISM: Artificial Sequence
<220> FEATURE:
<223> OTHER INFORMATION: functional penetrating peptide
<220> FEATURE:
<221> NAME/KEY: BINDING
<222> LOCATION: (1)..(1)
<223> OTHER INFORMATION: Ac-

<400> SEQUENCE: 3

Phe Ala Glu Lys Phe Lys Glu Ala Val Lys Asp Tyr Phe Ala Lys Phe
1               5              10             15

Trp Asp Gly Gly Arg Arg Arg Arg Arg Arg Arg Arg Pro Val Gly
            20              25              30

Leu Ile Gly Glu Gly Gly Glu Gly Gly Glu Gly Gly
        35              40

<210> SEQ ID NO 4
<211> LENGTH: 54
<212> TYPE: PRT
<213> ORGANISM: Artificial Sequence
<220> FEATURE:
<223> OTHER INFORMATION: functional penetrating peptide
<220> FEATURE:
<221> NAME/KEY: BINDING
<222> LOCATION: (1)..(1)
<223> OTHER INFORMATION: Ac-

<400> SEQUENCE: 4

Phe Ala Glu Lys Phe Lys Glu Ala Val Lys Asp Tyr Phe Ala Lys Phe
1               5              10             15

Trp Asp Gly Ser Gly Arg Arg Arg Arg Arg Arg Arg Arg Arg Arg
            20              25              30

Arg Arg Arg Arg Arg Arg Arg Pro Val Gly Leu Ile Gly Glu Gly Gly
        35              40              45

Glu Gly Gly Glu Gly Gly
    50

<210> SEQ ID NO 5
<211> LENGTH: 46
<212> TYPE: PRT
<213> ORGANISM: Artificial Sequence
<220> FEATURE:
<223> OTHER INFORMATION: functional penetrating peptide
<220> FEATURE:
<221> NAME/KEY: BINDING
<222> LOCATION: (1)..(1)
<223> OTHER INFORMATION: Ac-

<400> SEQUENCE: 5

Phe Ala Glu Lys Phe Lys Glu Ala Val Lys Asp Tyr Phe Ala Lys Phe
1               5              10             15

Trp Asp Gly Ser Gly Arg Arg Arg Arg Arg Arg Arg Arg Pro Val
            20              25              30

Gly Leu Ile Gly Glu Glu Glu Glu Glu Asp Asp Asp Asp Lys
        35              40              45
```

-continued

```
<210> SEQ ID NO 6
<211> LENGTH: 42
<212> TYPE: PRT
<213> ORGANISM: Artificial Sequence
<220> FEATURE:
<223> OTHER INFORMATION: functional penetrating peptide
<220> FEATURE:
<221> NAME/KEY: BINDING
<222> LOCATION: (1)..(1)
<223> OTHER INFORMATION: Ac-

<400> SEQUENCE: 6

Phe Ala Glu Lys Phe Lys Glu Ala Val Lys Asp Tyr Phe Ala Lys Phe
1               5                   10                  15

Trp Asp Gly Ser Gly Arg Arg Arg Arg Arg Arg Arg Arg Pro Val
            20                  25                  30

Gly Leu Ile Gly Glu Asp Asp Asp Asp Lys
        35                  40

<210> SEQ ID NO 7
<211> LENGTH: 62
<212> TYPE: PRT
<213> ORGANISM: Artificial Sequence
<220> FEATURE:
<223> OTHER INFORMATION: functional penetrating peptide
<220> FEATURE:
<221> NAME/KEY: BINDING
<222> LOCATION: (1)..(1)
<223> OTHER INFORMATION: Ac-

<400> SEQUENCE: 7

Phe Ala Glu Lys Phe Lys Glu Ala Val Lys Asp Tyr Phe Ala Lys Phe
1               5                   10                  15

Trp Asp Gly Ser Gly Arg Arg Arg Arg Arg Arg Arg Arg Gly Gly
            20                  25                  30

Gly Glu Arg Gly Pro Pro Gly Pro Gln Gly Ala Ala Arg Gly Phe Glx
        35                  40                  45

Gly Thr Pro Gly Leu Glu Gly Gly Glu Gly Gly Glu Gly Gly
    50                  55                  60

<210> SEQ ID NO 8
<211> LENGTH: 47
<212> TYPE: PRT
<213> ORGANISM: Artificial Sequence
<220> FEATURE:
<223> OTHER INFORMATION: functional penetrating peptide
<220> FEATURE:
<221> NAME/KEY: BINDING
<222> LOCATION: (1)..(1)
<223> OTHER INFORMATION: Ac-

<400> SEQUENCE: 8

Phe Ala Glu Lys Phe Lys Glu Ala Val Lys Asp Tyr Phe Ala Lys Phe
1               5                   10                  15

Trp Asp Gly Ser Gly Arg Arg Arg Arg Arg Arg Arg Arg Gly Pro
            20                  25                  30

Leu Gly Leu Leu Gly Cys Glu Gly Gly Glu Gly Gly Glu Gly Gly
        35                  40                  45

<210> SEQ ID NO 9
<211> LENGTH: 21
<212> TYPE: PRT
<213> ORGANISM: Artificial Sequence
<220> FEATURE:
```

-continued

```
<223> OTHER INFORMATION: peptide chain linking a nanocarrier end
<220> FEATURE:
<221> NAME/KEY: BINDING
<222> LOCATION: (1)..(1)
<223> OTHER INFORMATION: Ac-

<400> SEQUENCE: 9

Phe Ala Glu Lys Phe Lys Glu Ala Val Lys Asp Tyr Phe Ala Lys Phe
1               5                   10                  15

Trp Asp Gly Ser Gly
            20

<210> SEQ ID NO 10
<211> LENGTH: 22
<212> TYPE: PRT
<213> ORGANISM: Artificial Sequence
<220> FEATURE:
<223> OTHER INFORMATION: peptide chain linking a nanocarrier end
<220> FEATURE:
<221> NAME/KEY: BINDING
<222> LOCATION: (1)..(1)
<223> OTHER INFORMATION: Ac-

<400> SEQUENCE: 10

Phe Ala Glu Lys Phe Lys Glu Ala Val Lys Asp Tyr Phe Ala Lys Phe
1               5                   10                  15

Trp Asp Gly Ala Gly Ala
            20

<210> SEQ ID NO 11
<211> LENGTH: 20
<212> TYPE: PRT
<213> ORGANISM: Artificial Sequence
<220> FEATURE:
<223> OTHER INFORMATION: peptide chain linking a nanocarrier end
<220> FEATURE:
<221> NAME/KEY: BINDING
<222> LOCATION: (1)..(1)
<223> OTHER INFORMATION: Ac-

<400> SEQUENCE: 11

Phe Ala Glu Lys Phe Lys Glu Ala Val Lys Asp Tyr Phe Ala Lys Phe
1               5                   10                  15

Trp Asp Gly Gly
            20

<210> SEQ ID NO 12
<211> LENGTH: 9
<212> TYPE: PRT
<213> ORGANISM: Artificial Sequence
<220> FEATURE:
<223> OTHER INFORMATION: arginine-rich amino acid sequence

<400> SEQUENCE: 12

Arg Arg Arg Arg Arg Arg Arg Arg Arg
1               5

<210> SEQ ID NO 13
<211> LENGTH: 18
<212> TYPE: PRT
<213> ORGANISM: Artificial Sequence
<220> FEATURE:
<223> OTHER INFORMATION: arginine-rich amino acid sequence

<400> SEQUENCE: 13

Arg Arg Arg Arg Arg Arg Arg Arg Arg Arg Arg Arg Arg Arg Arg Arg
1               5                   10                  15
```

Arg Arg

<210> SEQ ID NO 14
<211> LENGTH: 6
<212> TYPE: PRT
<213> ORGANISM: Artificial Sequence
<220> FEATURE:
<223> OTHER INFORMATION: matrix metalloproteinase-9 sensitive peptide

<400> SEQUENCE: 14

Pro Val Gly Leu Ile Gly
1               5

<210> SEQ ID NO 15
<211> LENGTH: 23
<212> TYPE: PRT
<213> ORGANISM: Artificial Sequence
<220> FEATURE:
<223> OTHER INFORMATION: matrix metalloproteinase-9 sensitive peptide

<400> SEQUENCE: 15

Gly Gly Gly Glu Arg Gly Pro Pro Gly Pro Gln Gly Ala Ala Arg Gly
1               5                   10                  15

Phe Glx Gly Thr Pro Gly Leu
            20

<210> SEQ ID NO 16
<211> LENGTH: 8
<212> TYPE: PRT
<213> ORGANISM: Artificial Sequence
<220> FEATURE:
<223> OTHER INFORMATION: matrix metalloproteinase-9 sensitive peptide

<400> SEQUENCE: 16

Gly Pro Leu Gly Leu Leu Gly Cys
1               5

<210> SEQ ID NO 17
<211> LENGTH: 9
<212> TYPE: PRT
<213> ORGANISM: Artificial Sequence
<220> FEATURE:
<223> OTHER INFORMATION: polyanion inhibitory peptide

<400> SEQUENCE: 17

Glu Gly Gly Glu Gly Gly Glu Gly Gly
1               5

<210> SEQ ID NO 18
<211> LENGTH: 6
<212> TYPE: PRT
<213> ORGANISM: Artificial Sequence
<220> FEATURE:
<223> OTHER INFORMATION: polyanion inhibitory peptide

<400> SEQUENCE: 18

Glu Asp Asp Asp Asp Lys
1               5

<210> SEQ ID NO 19
<211> LENGTH: 10
<212> TYPE: PRT
<213> ORGANISM: Artificial Sequence
<220> FEATURE:
<223> OTHER INFORMATION: polyanion inhibitory peptide -continued

```
<400> SEQUENCE: 19

Glu Glu Glu Glu Glu Asp Asp Asp Asp Lys
1               5                   10

<210> SEQ ID NO 20
<211> LENGTH: 60
<212> TYPE: PRT
<213> ORGANISM: Artificial Sequence
<220> FEATURE:
<223> OTHER INFORMATION: functional penetrating peptide
<220> FEATURE:
<221> NAME/KEY: BINDING
<222> LOCATION: (1)..(1)
<223> OTHER INFORMATION: Ac-

<400> SEQUENCE: 20

Phe Ala Glu Lys Phe Lys Glu Ala Val Lys Asp Tyr Phe Ala Lys Phe
1               5                   10                  15

Trp Asp Gly Ser Gly Arg Arg Arg Arg Arg Arg Arg Arg Gly Glu
            20                  25                  30

Arg Gly Pro Pro Gly Pro Gln Gly Ala Ala Arg Gly Phe Glx Gly Thr
            35                  40                  45

Pro Gly Leu Glu Gly Gly Glu Gly Gly Glu Gly Gly
    50                  55                  60

<210> SEQ ID NO 21
<211> LENGTH: 30
<212> TYPE: PRT
<213> ORGANISM: Artificial Sequence
<220> FEATURE:
<223> OTHER INFORMATION: functional penetrating peptide
<220> FEATURE:
<221> NAME/KEY: BINDING
<222> LOCATION: (1)..(1)
<223> OTHER INFORMATION: Ac-

<400> SEQUENCE: 21

Phe Ala Glu Lys Phe Lys Glu Ala Val Lys Asp Tyr Phe Ala Lys Phe
1               5                   10                  15

Trp Asp Gly Ser Gly Arg Arg Arg Arg Arg Arg Arg Arg
            20                  25                  30

<210> SEQ ID NO 22
<211> LENGTH: 40
<212> TYPE: PRT
<213> ORGANISM: Artificial Sequence
<220> FEATURE:
<223> OTHER INFORMATION: functional penetrating peptide
<220> FEATURE:
<221> NAME/KEY: BINDING
<222> LOCATION: (1)..(1)
<223> OTHER INFORMATION: Ac-

<400> SEQUENCE: 22

Phe Ala Glu Lys Phe Lys Glu Ala Val Lys Asp Tyr Phe Ala Lys Phe
1               5                   10                  15

Trp Asp Gly Ala Gly Ala Arg Arg Arg Arg Arg Arg Arg Arg Arg
            20                  25                  30

Arg Arg Arg Arg Arg Arg Arg Arg
        35                  40

<210> SEQ ID NO 23
<211> LENGTH: 44
<212> TYPE: PRT
<213> ORGANISM: Artificial Sequence
```

-continued

```
<220> FEATURE:
<223> OTHER INFORMATION: functional penetrating peptide
<220> FEATURE:
<221> NAME/KEY: BINDING
<222> LOCATION: (1)..(1)
<223> OTHER INFORMATION: Ac-

<400> SEQUENCE: 23

Phe Ala Glu Lys Phe Lys Glu Ala Val Lys Asp Tyr Phe Ala Lys Phe
1               5                   10                  15

Trp Asp Gly Gly Arg Arg Arg Arg Arg Arg Arg Arg Arg Arg Arg
            20                  25                  30

Arg Arg Arg Arg Arg Arg Pro Val Gly Leu Ile Gly
        35                  40
```

LIPID NANO DRUG DELIVERY SYSTEM TARGETING BRAIN LESION AND PREPARATION METHOD AND APPLICATION THEREOF

REFERENCE TO SEQUENCE LISTING

The Sequence Listing is submitted concurrently with the specification as an ASCII formatted text file via EFS-Web, with a file name of "P22410401US-2-SEQ", a creation date of Apr. 22, 2022, and a size of 10,184 bytes. The Sequence Listing filed via EFS-Web is part of the specification and is incorporated in its entirety by reference herein.

The present application is a National Stage of International Application No. PCT/CN2020/128748, filed on Nov. 13, 2020, which claims priority of the Chinese Patent Application No. CN201911157549.0 filed on Nov. 22, 2019, the contents of which are incorporated herein by reference in their entireties.

TECHNICAL FIELD

The present invention belongs to the field of technology of nano biomedical material technique-nano drugs and drug delivery systems, in particular to a lipid nano drug delivery system targeting brain lesion and preparation method and application thereof.

BACKGROUND

Traumatic brain injury (TBI) is a common disease in neurosurgery, and its high mortality and disability rate brings great economic and psychological burdens to patients' families. It is currently believed that TBI injuries can be divided into two categories: primary injury and secondary injury, wherein primary injury is a brain parenchymal injury caused by mechanical injury, which occurs mainly at the point of external force. However, in addition to the damage to the brain at the moment of injury, early mechanical injury often induces secondary injury cascade reactions, including cellular excitotoxicity, vasogenic and cytotoxic edema, hypoxia-ischemia, mitochondrial dysfunction, oxidative stress and inflammation, which exacerbate the damage to the original impaired tissue. Due to the lack of effective treatments, many brain injury patients got varying degrees of neurological dysfunction after recovery of consciousness, and there is a lack of specific treatment options on how to improve the neurological dysfunction caused by traumatic brain injury.

The pathophysiological mechanisms of TBI neurological dysfunction are various and complex, the core of which is the dysregulation of calcium homeostasis. The initial mechanical injury causes destruction of cell membranes and cytoskeletal elements, then the intracellular calcium increases. The excessive intracellular calcium stimulates the opening of mitochondrial permeability transition pores, which increases the permeability of mitochondrial membrane, leading to mitochondrial edema and rupture, and causing apoptosis; the calcium dysregulation also causes glutamate toxicity, edema, high expression of matrix metalloproteinases and release of inflammatory cytokines. These cascade events ultimately lead to the death of brain parenchyma cells. Therefore, mitochondria play an important role in maintaining intracellular homeostasis and cytopathological conditions. In recent years, mitochondria, as the core mediators of the secondary injury cascade response, have been considered as effective targets for preventing cell death and dysfunction after TBI.

At present, a variety of neuroprotective drugs targeting mitochondria have been identified, among which cyclosporine A (CsA) has been widely studied. CsA, a neutral cyclic peptide containing 11 amino acids isolated from fungi, has been approved by FDA and widely used as an immunosuppressant in organ transplantation. Previous studies have found that CsA maintains the integrity of mitochondrial function by inhibiting the opening of mitochondrial mPTP, which reduces the uptake of mitochondrial calcium and the production of ROS mediated by excitatory toxicity. Thus, the oxygen utilization of brain tissue is improved after TBI. Therefore, CsA has been considered as a potential neuroprotective drug to enter clinical trials. However, due to the poor water solubility and high binding rate to plasma proteins of CsA, it is difficult for CsA to cross the blood-brain barrier. Because the therapeutic window of CsA is narrow, when administrating CsA orally, neuroprotective effect can be achieved only with high dose. In the condition of high dose and chronic administration, systemic level of cyclosporine A has restrictive side effects, such as immunosuppression, hepatotoxicity and nephrotoxicity, thus limiting its clinical application.

Content of the Present Invention

The first purpose of the present invention is to provide a lipid nano drug delivery system targeting brain lesion, which can target the brain lesion and achieve mitochondrial enrichment through the modification of the functional penetrating peptide.

The second purpose of the present invention is to provide a use of the lipid nano drug delivery system targeting brain lesion in preparing a medicament for the treatment of brain injury disease.

The third purpose of the present invention is to provide a functional penetrating peptide for modifying a lipid nano drug delivery system targeting brain lesion, which targeting brain lesion.

The fourth purpose of the present invention is to provide a use of the functional penetrating peptide for modifying a lipid nano drug delivery system targeting brain lesion in preparing the lipid nano drug delivery system targeting brain lesion.

The fifth purpose of the present invention is to provide a preparation method of the lipid nano drug delivery system targeting brain lesion, wherein the delivery drug is cyclosporin A prepared by a dilution-induced precipitation.

In order to achieve the first purpose, the present invention provides a lipid nano drug delivery system targeting brain lesion, wherein the drug delivery system comprises lipids, a delivery drug and a functional penetrating peptide, and the functional penetrating peptide is formed by covalently conjugating a peptide chain that incorporates into the nanocarrier, an arginine-rich penetrating peptide, a matrix metalloproteinase-9 sensitive peptide and a polyanion inhibitory peptide.

As a preferred solution, the functional penetrating peptide has a sequence of one of the following peptides with terminal acetylation:

(SEQ ID NO: 1)
Ac-FAEKFKEAVKDYFAKFWD-GSG-RRRRRRRRR-PVGLIG-
EGGEGGEGG,

3

-continued (SEQ ID NO: 2)
Ac-FAEKFKEAVKDYFAKFWD-GAGA-RRRRRRRRR-PVGLIG-
EGGEGGEGG, (SEQ ID NO: 3)
Ac-FAEKFKEAVKDYFAKFWD-GG-RRRRRRRRR-PVGLIG-
EGGEGGEGG, (SEQ ID NO: 4)
Ac-FAEKFKEAVKDYFAKFWD-GSG-RRRRRRRRRRRRRRRRR-
PVGLIG-EGGEGGEGG, (SEQ ID NO: 5)
Ac-FAEKFKEAVKDYFAKFWD-GSG-RRRRRRRRR-PVGLIG-
EEEEEDDDDK, (SEQ ID NO: 6)
Ac-FAEKFKEAVKDYFAKFWD-GSG-RRRRRRRRR-PVGLIG-
EDDDDK, (SEQ ID NO: 7)
Ac-FAEKFKEAVKDYFAKFWD-GSG-RRRRRRRRR-
GGGERGPPGPQGAARGFZGTPGL-EGGEGGEGG, (SEQ ID NO: 8)
Ac-FAEKFKEAVKDYFAKFWD-GSG-RRRRRRRRR-GPLGLLGC-
EGGEGGEGG.

As a preferred solution, the functional penetrating peptide has a mass ratio of 1:10-1:300 to the lipid, preferably 1:100.

As a preferred solution, the delivery drug comprises cyclosporine A, vasoactive peptides, enkephalins, endorphins, neurotensin and Sandimmun Neoral.

As a further preferred solution, the delivery drug is cyclosporine A, and the cyclosporine A is prepared by a dilution-induced precipitation. The mitochondria are repaired by encapsulating peptide drug cyclosporin A with a lipid nanoparticle core by a dilution-induced precipitation, thereby solving the current problems that cyclosporin A is difficult to effectively reach a brain lesion and the therapeutic window is small, which improves the ability of CsA to repair cells around the brain lesion with a small administration dose (equivalent to about one-sixteenth of the dose of unmodified CsA).

As a further preferred solution, the cyclosporine A has a mass ratio of 1:1-1:100 to the lipid, preferably 1:4.

In order to achieve the second purpose, the present invention provides a use of the lipid nano drug delivery system targeting brain lesion in preparing a medicament for the treatment of brain injury disease.

In order to achieve the third purpose, the present invention provides a functional penetrating peptide for modifying a lipid nano drug delivery system targeting brain lesion, wherein the functional penetrating peptide has a sequence of one of the following peptides with terminal acetylation:

(SEQ ID NO: 1)
Ac-FAEKFKEAVKDYFAKFWD-GSG-RRRRRRRRR-PVGLIG-
EGGEGGEGG, (SEQ ID NO: 2)
Ac-FAEKFKEAVKDYFAKFWD-GAGA-RRRRRRRRR-PVGLIG-
EGGEGGEGG, (SEQ ID NO: 3)
Ac-FAEKFKEAVKDYFAKFWD-GG-RRRRRRRRR-PVGLIG-
EGGEGGEGG, (SEQ ID NO: 4)
Ac-FAEKFKEAVKDYFAKFWD-GSG-RRRRRRRRRRRRRRRRR-
PVGLIG-EGGEGGEGG,

4

-continued (SEQ ID NO: 5)
Ac-FAEKFKEAVKDYFAKFWD-GSG-RRRRRRRRR-PVGLIG-
EEEEEDDDDK, (SEQ ID NO: 6)
Ac-FAEKFKEAVKDYFAKFWD-GSG-RRRRRRRRR-PVGLIG-
EDDDDK, (SEQ ID NO: 7)
Ac-FAEKFKEAVKDYFAKFWD-GSG-RRRRRRRRR-
GGGERGPPGPQGAARGFZGTPGL-EGGEGGEGG, (SEQ ID NO: 8)
Ac-FAEKFKEAVKDYFAKFWD-GSG-RRRRRRRRR-GPLGLLGC-
EGGEGGEGG.

In order to achieve the fourth purpose, the present invention provides a use of the functional penetrating peptide for modifying a lipid nano drug delivery system targeting brain lesion in preparing the lipid nano drug delivery system targeting brain lesion.

In order to achieve the fifth purpose, the present invention provides a preparation method of the lipid nano drug delivery system targeting brain lesion, wherein the preparation method comprises a stepwise method or a one-step method, wherein the stepwise method comprises following steps:

a) prepare the precipitated solution of cyclosporin A by a dilution-induced precipitation;

b) prepare a cyclosporine A-loaded lipid nano drug delivery system;

c) prepare the cyclosporine A-loaded lipid nano drug delivery system modified with the functional penetrating peptide, by adding the functional penetrating peptide into the lipid nano drug delivery system solution prepared in step b) above.

The one-step method refers to that a cyclosporine A-loaded lipid nano drug delivery system modified with the functional penetrating peptide is directly prepared by self-assembly of lipid, cyclosporine A and the functional penetrating peptide through microfluidic chip.

As a preferred solution, the induced precipitation of step a) is implemented by microfluidics, the precipitate is formed by passing an aqueous phase and an alcohol phase containing cyclosporine A through microfluidic chip pipeline, and preferably the alcohol phase has a volume ratio of 1:1-1:100 to the aqueous phase, and the preferred ratio is 1:8.

As a preferred solution, the cyclosporine A-loaded lipid nano drug delivery system of step b) is prepared by a continuous flow technique of microfluidics, and the cyclosporine A-loaded lipid nano drug delivery system is obtained by self-assembly of the cyclosporine A and a lipid-containing phase through microfluidic pipeline, wherein the cyclosporine A is prepared by the microfluidic induced precipitation.

The peptide chain linking a nanocarrier end refers to an amino acid sequence designed to mimic linkage to a lipid nano drug delivery system, wherein the peptide chain that incorporates into the nanocarrier comprises but not limited to:

(SEQ ID NO: 9)
Ac-FAEKFKEAVKDYFAKFWD-GSG, (SEQ ID NO: 10)
Ac-FAEKFKEAVKDYFAKFWD-GAGA, (SEQ ID NO. 11)
Ac-FAEKFKEAVKDYFAKFWD-GG.

5

The arginine-rich penetrating peptide refers to an arginine-rich amino acid sequence, wherein the arginine-rich amino acid sequence comprises, but not limited to:

(SEQ ID NO. 12)

RRRRRRRRR, (SEQ ID NO. 13)

RRRRRRRRRRRRRRRRR.

The matrix metalloproteinase-9 sensitive peptide refers to an amino acid sequence, which is hydrolyzed and digested by the overexpressed MMP-9 specifically located at brain injury sites, including but not limited to:

(SEQ ID NO: 14)

PVGLIG, (SEQ ID NO: 15)

GGGERGPPGPQGAARGFZGTPGL, (SEQ ID NO: 16)

GPLGLLGC.

The polyanion inhibitory peptide is an amino acid sequence riches in acidic amino acids, including but not limited to:

(SEQ ID NO: 17)

EGGEGGEGG, (SEQ ID NO: 18)

EDDDDK, (SEQ ID NO: 19)

EEEEEEDDDDK.

The lipid is one or more of lecithin, soybean phospholipids, phosphatidylcholine, phosphatidylethanolamine, phosphatidylserine, phosphatidylglycerol, phosphatidylinositol, phosphatidic acid, cardiolipin, lysophospholipids, sphingosine, ceramide, sphingomyelin, cerebroside, monosialotetrahexosylganglioside, and derivatives thereof.

The induced precipitation can be microfluidics, reverse microemulsion or salting-out. The microfluidics is preferred in the present application, where the precipitate is formed by passing an aqueous phase and an oil phase containing cyclosporine A through a microfluidic chip pipeline.

The present invention adopts lipid nanocarriers and uses the dilution-induced precipitation technique to encapsulate CsA in the core for brain drug delivery, which can effectively solve the problem that CsA is insoluble in water and difficult to cross the blood-brain barrier. In order to realize the targeted delivery of nanocarriers to the brain injury sites, the present invention further designs a functional penetrating peptide with matrix metalloproteinase-9 sensitivity to modify the CsA-loaded lipid nanocarriers. The functional penetrating peptide consists of the following components: an α-helical peptide in front connecting the nanocarrier and the functional penetrating peptide, an arginine-rich penetrating peptide composed of a plurality of arginine that facilitates the entry of nanocarrier into the cell; a matrix metalloproteinase-9 sensitive peptide designed to connect to the penetrating peptide due to the arginine oligopeptide's low specificity for cells due to its high positive charge, which is intended to be hydrolyzed and digested by the overexpressed matrix metalloproteinase-9 located specifically at brain injury sites, exposing the arginine-rich penetrating peptide that further leads the nanocarrier into the cells at the injury sites, thereby enabling the brain lesion-targeting delivery of the nanocarriers; and a polyanion inhibitory peptide at the tail to keep the positive charge of the arginine oligopeptide blocked during the circulation through the interaction between the positive and negative charges, which enhances the stability of the functional penetrating peptide.

The advantage of the present invention is that the lipid nano drug delivery system can target the brain lesion and achieve mitochondrial enrichment through the modification of the functional penetrating peptide. The mitochondria are repaired by encapsulating peptide drug cyclosporin A with a lipid nanoparticle core by a dilution-induced precipitation, thereby solving the current problems that cyclosporin A is difficult to effectively reach a brain lesion and the therapeutic window is small, which improves the ability of CsA to repair cells around the brain lesion with a small administration dose (equivalent to about one-sixteenth of the dose of unmodified CsA).

DETAILED DESCRIPTION OF THE PREFERRED EMBODIMENT

Figure 1:
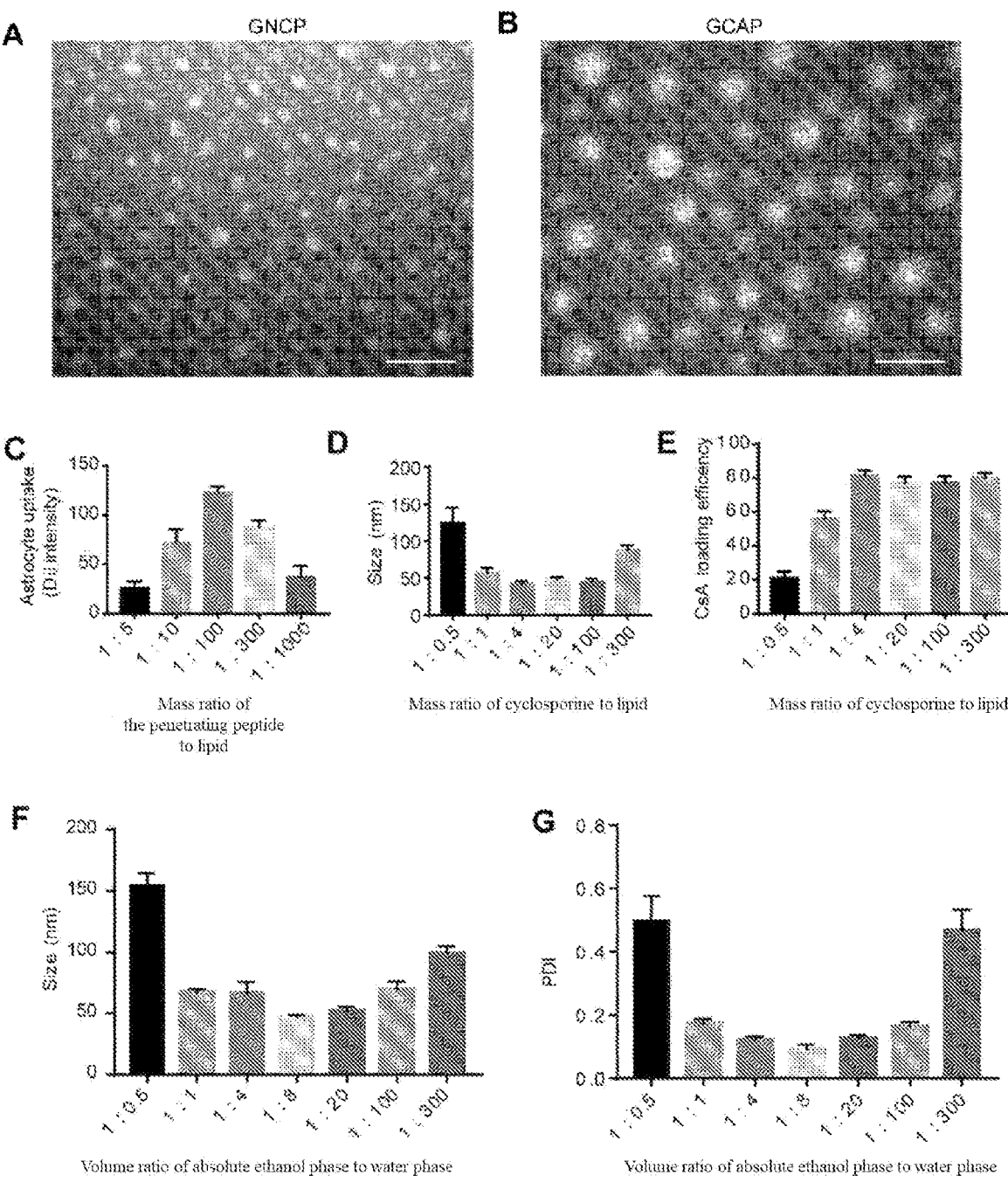
FIG. 1 shows: A shows the morphology of the functional penetrating peptide-modified lipid nano drug delivery system (liposomes) loaded with cyclosporine A under a transmission electron microscope, and B shows the morphology of the functional penetrating peptide-modified lipid nano drug delivery system (liposomes) unloaded with CsA. Scale bar: 50 nm. C shows the difference in astrocyte uptake of liposomes containing different amounts of the penetrating peptide. D and E show the effect of cyclosporin A input ratio on the nanostructure and drug loading of the cyclosporine A-loaded lipid nano drug delivery system. F and G shows the effect of the volume ratio between anhydrous ethanol phase and water phase on the nanostructure.

The present invention is further illustrated below by examples. It should be understood that the following examples are only intended to assist those skilled in the art in understanding the present invention, and the present invention is not limited thereto.

Example 1. Preparation and Characterization of the Functional Penetrating Peptide-Modified Cyclosporine A-Loaded Lipid Nano Drug Delivery System (1) Preparation Blank liposome was prepared by thin-film hydration method. 2 mg of ganglioside (GM1) was dissolved with 2 ml mixture chloroform and methanol at a ratio of 2:1 to obtain 1 mg/mL of ganglioside stock solution. 3.6 mg of lipid (e.g. DMPC) was added to a 500 ml round bottom flask, 400 μl of the ganglioside stock solution was added, then 3 mL of chloroform was added, followed by evacuating the flask using a rotary evaporator for 1 h. 1 mg, 2 mg and 4 mg of cyclosporin A (CsA) was dissolved with 2 ml-4 ml of anhydrous ethanol to obtain stock solutions of 1 mg/ml CsA. The CsA peptide precipitation solution was prepared by diluting 40 μl-4 ml of the CsA stock solution to 4 ml with ultrapure water. The CsA peptide precipitation solution prepared above was added to the round bottom flask with lipid film to hydrate the lipid, then the round bottom flask was placed on a shaker at 200 rpm, 37° C. for 2 h until the film hydrated off to obtain liposome loaded with CsA solid core. The water bath probe sonication (1% power, 5 min) was used to further reduce the size of liposome particle. The precipitated CsA peptide particles which were not encapsulated into the liposome were removed from the GCA by separation and filtration using a 0.22 μm hydrophilic PTFE syringe filter. The functional penetrating peptide was added to the liposome loaded with CsA solid core at 1/100 of the total lipid weight and incubated overnight at 4° C. on a shaker at 200 rpm to obtain the functional penetrating peptide-modified liposome loaded with CsA solid core (GCAP).

The solid phase peptide synthesis method was used to synthesize the following functional peptides:

```
                                    (SEQ ID NO: 1)
Ac-FAEKFKEAVKDYFAKFWD-GSG-RRRRRRRRR-PVGLIG-
EGGEGGEGG, (SEQ ID NO: 2)
Ac-FAEKFKEAVKDYFAKFWD-GAGA-RRRRRRRRR-PVGLIG-
EGGEGGEGG, (SEQ ID NO: 3)
Ac-FAEKFKEAVKDYFAKFWD-GG-RRRRRRRRR-PVGLIG-
EGGEGGEGG, (SEQ ID NO: 4)
Ac-FAEKFKEAVKDYFAKFWD-GSG-RRRRRRRRRRRRRRRRR-
PVGLIG-EGGEGGEGG, (SEQ ID NO: 5)
Ac-FAEKFKEAVKDYFAKFWD-GSG-RRRRRRRRR-PVGLIG-
EEEEEDDDDK, (SEQ ID NO: 6)
Ac-FAEKFKEAVKDYFAKFWD-GSG-RRRRRRRRR-PVGLIG-
EDDDDK, (SEQ ID NO: 7)
Ac-FAEKFKEAVKDYFAKFWD-GSG-RRRRRRRRR-
GGGERGPPGPQGAARGFZGTPGL-EGGEGGEGG, (SEQ ID NO: 8)
Ac-FAEKFKEAVKDYFAKFWD-GSG-RRRRRRRRR-GPLGLLGC-
EGGEGGEGG.
```

The specific method for the preparation of the peptides: the corresponding amino acids were conjugated to a chloromethyl polystyrene resin, and the amino protection group was removed under the protection of trifluoroacetic acid. The peptide conjugated to the resin was hydrolyzed with hydrogen fluoride, then precipitated in ether ice bath. After dissolving the precipitate in acetonitrile, the solution was subjected to rotary evaporation. The peptide was further purified in an acetonitrile-water system.

(2) Characterization

The functional penetrating peptide-modified cyclosporine A-loaded lipid nano drug delivery system was negatively stained with phosphotungstic acid for 5 minutes and the morphology was observed under a transmission electron microscope at 80 kV. As shown in FIG. 1, under a transmission electron microscope, the functional penetrating peptide-modified cyclosporine A-loaded lipid nano drug delivery system (A) was rounder and smoother in appearance, significantly larger and uniform in particle size, and good in dispersibility as compared with the functional penetrating peptide-modified drug-unloaded lipid nano drug delivery system (B), indicating that CsA drugs were successfully encapsulated.

(3) Selection of the Ratio of the Penetrating Peptide to Lipid

The cyclosporine A-loaded lipid nano drug delivery systems at the ratios of the penetrating peptide (SEQ ID NO: 1) to lipid of 1:5, 1:10, 1:100, 1:300 and 1:1000 were prepared through the same way as in step (1) of this Example, and red fluorescent probe DiI (accounting for 1% of the lipid mass) was added at the time of lipid film formation.

The primary astrocytes were cultured in 96-well plates, incubated with the above lipid nano drug delivery systems at different ratios of the penetrating peptide at 37° C. for 3 h, and then fixed in 3.7% formaldehyde for 10 minutes. After staining the nuclear with DAPI, the uptake of the preparations into the cells was analyzed through a high-definition drug analysis system. As shown in C of FIG. 1, the levels of the cellular uptake of nano drug delivery systems in astrocytes is higher at the ratios of the penetrating peptide to lipid from 1:10 to 1:300, wherein 1:100 is the optimal ratio.

(4) Selection of the Ratio of Cyclosporine a to Lipid

The cyclosporine A-loaded lipid nano drug delivery systems at the ratios of cyclosporine to lipid of 1:0.5, 1:1, 1:4, 1:20, 1:100 and 1:300 were prepared through the same way as in step (1) of this Example. The particle size of each formulation was analyzed through a laser particle size analyzer, and the results showed at the cyclosporine to lipid ratios of 1:1-1:100, nanostructure with smaller particle size was obtained (as shown in D of FIG. 1). The encapsulation rate of cyclosporin A was determined by high performance liquid chromatography, and the results showed that the systems at the cyclosporine to lipid ratios of 1:1-1:300 obtained better encapsulation rate (as shown in E of FIG. 1), while the systems at the cyclosporine to lipid ratio of 1:300 exhibited a drug loading capacity of only about 0.27%, which was too low to achieve sufficient drug concentration for the subsequent experiments in vivo. Therefore, the optimal cyclosporine to lipid ratios are 1:1-1:100, wherein 1:4 is the optimal ratio.

(5) Selection of the Volume Ratio of Anhydrous Ethanol Phase to Aqueous Phase

The cyclosporine A-loaded lipid nano drug delivery systems at the volume ratios of the anhydrous ethanol phase containing cyclosporine to the aqueous phase of the liposome solution of 1:0.5, 1:1, 1:4, 1:20, 1:8, 1:100 and 1:300 were prepared through the same way as in step (4) of this Example. The particle size of each formulation and the polydiseperse index (PDI) of particle size were analyzed through a laser particle size analyzer, and the results showed that nanostructures with smaller and uniform particle size were prepared at the volume ratios of anhydrous ethanol phase to aqueous phase of 1:1-1:100, (as shown in F, G of FIG. 1), wherein 1:8 is the optimal ratio.

Example 2. The Uptake of Functional Penetrating Peptide-Modified Cyclosporine A-Loaded Lipid Nano Drug Delivery System into Primary Astrocytes and their Co-Localization with Mitochondria (1) Preparation The drug-loaded liposome was prepared via the thin-film hydration method as described in Example 1, the fluorescent dye DiI (20-100 μg) was added into a 500 ml round-bottom flask when preparing the lipid film, and then the functional penetrating peptide-modified cyclosporine A-loaded lipid nano drug delivery system was prepared through the same way as described in Example 1. 1 mg/ml of the functional penetrating peptide (SEQ ID NO: 3) was added into the liposome loaded with CsA solid core at ratios of 1/30 and 1/100 of the total lipid weight, then the mixture was placed in a shaker at 200 rpm, and incubated overnight at 4° C. to obtain the fluorescence-labeled functional penetrating peptide-modified cyclosporine A-loaded lipid nano drug delivery system, and the effects of the different ratios of the functional penetrating peptide on the targeting efficiency were evaluated.

(2) The primary astrocytes were isolated in a vertical flow clean bench. Within 24 hours after birth, neonatal SD rats were sterilized with alcohol cotton and euthanized through cervical dislocation, and the brain was divided into two halves along the brain's midline. The skull as well as the meninges were stripped to isolate the hippocampal tissue. The vascular membrane and other brain tissues were carefully stripped under a microscope. The isolated hippocampal tissue was cut up and digested with digestive juice at 37° C. for 10-15 min. After digestion, the digestive liquid was transferred to a centrifuge tube containing 10 ml complete culture medium to stop digestion. Next, 20 μL DNA enzyme was added and gently blown 15-20 times to disperse the cells. Then the tube was centrifuged at 1500 rpm for 15 min. The supernatant was discarded to obtain the precipitate, which was added with complete culture medium, the precipitate was blowed and mixed well to obtain cell suspension. The cells were counted under a microscope, then diluted to the appropriate concentration with complete culture medium, and inoculated into a poly-Lysine coated 96-well plates at a density of $1\times10^4$ cells/well. The plate was incubated in a 5% $CO_2$ cell incubator at 37° C.

Next, the primary astrocytes were inoculated into a well plate and incubated with 20 μg/ml lipid mass of cyclosporine A-loaded lipid nano drug delivery system modified at different ratios of the functional penetrating peptide, wherein the cyclosporine A-loaded lipid nano drug delivery system was loaded with fluorescence probe DiI. After incubation for 3 hours, 500 ng/ml MMP protein and mitochondrial indicator Mitotracker were added. Then the primary astrocytes were washed once with PBS and fixed with paraformaldehyde. After staining the nuclear, the primary astrocytes were examined under a laser confocal microscope to detect the fluorescence intensity of the uptake of functional penetrating peptide-modified cyclosporine A-loaded lipid nano drug delivery system into primary astrocytes and their co-localization with mitochondria.

Figure 2:
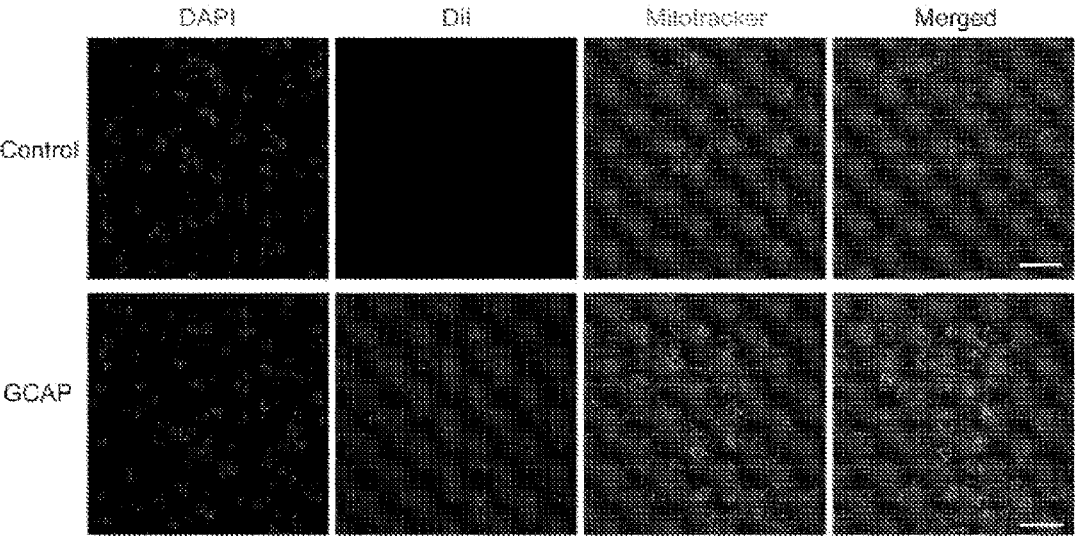
FIG. 2 shows the uptake of functional penetrating peptide-modified cyclosporine A-loaded lipid nano drug delivery system (GCAP) in primary astrocytes and their co-localization with mitochondrial markers. Scale bar: 50 μm.

As shown in FIG. 2, the functional penetrating peptide-modified cyclosporine A-loaded lipid nano drug delivery system loaded with fluorescence probe was highly co-localized with the mitochondrial indicator Mitotracker, indicating that the functional penetrating peptide-modified cyclosporine A-loaded lipid nano drug delivery system could be delivered to mitochondria effectively.

Example 3. Protection Effect of the Functional Penetrating Peptide-Modified Cyclosporine A-Loaded Lipid Nano Drug Delivery System on Microglia and Neurons In Vitro (1) Preparation The preparation of the functional penetrating peptide (SEQ ID NO: 8)-modified cyclosporine A-loaded lipid nano drug delivery system was optimized by microfluidics. 40 μl-4 ml of anhydrous ethanol phase containing 3.6 mg DMPC lipid and 0.4 mg of ganglioside was prepared, as well as 4-10 ml of ethanol containing 1 mg, 2 mg and 4 mg of cyclosporine A, and 10 ml of aqueous phase containing the functional penetrating peptide. The flow rate ratio was set to a total flow rate of 5 ml/min for the entry of solutions into the microfluidic chip to obtain the solution of the functional penetrating peptide-modified cyclosporine A-loaded lipid nano drug delivery system, and the solution was replaced with aqueous solution with dialysis and then filtered.

(2) Microglia (BV2) were cultured in 96-well plates. The culture medium was replaced with Earle's balanced salt solution without glucose after culturing the Microglia for 2 h in hypoxic environment (37° C., 5% $CO_2$, 95% $N_2$). Another 2 h later, the solution was replaced with normal neuronal culture medium to establish an oxygen-glucose deprivation cell model which was used to simulate the cellular state in the brain after brain injury. The cells were administrated with culture medium-DMEM, 2.5 μg/ml of CsA in the low CsA concentration group, 12.5 μg/ml of CsA in the high CsA concentration group, 2.5 μg/ml of the functional penetrating peptide-modified cyclosporine A-loaded lipid nano drug delivery system (GCAP) in the low GCAP concentration group and 12.5 μg/ml of GCAP in the high GCAP concentration group, with each concentration in sextuplicate. After culturing the cells for 3 h, mitochondria were isolated. Cells were washed once with PBS, then digested with trypsin, followed by centrifuging at room temperature for 5-10 min to collect the cells. After gently resuspending the cell precipitate with ice bath pre-cooled PBS, a small number of cells was taken for counting, then the remaining cells were centrifuged at 600 g for 5 min at 4° C. to be precipitated. After discarding the supernatant, the remaining 20-50 million cells were gently suspended by adding with 1-2.5 ml of mitochondrial isolation reagent or mitochondrial isolation reagent added with protease inhibitor (PMSF) before use, and the suspended cells were placed in an ice bath for 10-15 minutes. The cell suspension was then transferred into a glass homogenizer and homogenized for about 10-30 times. The homogenized cells were centrifuged at 4° C., 600 g for 10 minutes, then the supernatant was transferred to another centrifuge tube and centrifuged at 4° C., 11,000 g for 10 minutes. The precipitate of the isolated cellular mitochondria was obtained by discarding the supernatant carefully. The prepared JC-1 staining working solution was diluted 5 times with JC-1 staining buffer. 0.1 ml of the purified mitochondria with a total content of 10-100 μg protein was added to 0.9 ml of the 5 times diluted JC-1 staining working solution. The mitochondria stained with JC-1 were detected through a fluorescent microplate reader, with the excitation light/emission light of 490 nm/530 nm for the detection of JC-1 monomer, and with the excitation light/emission light of 525 nm/590 nm for the detection of JC-1 polymer.

After treated in NMDA (100 μmol/L) and glycine (10 μmol/L) solutions for 2 h, the neuronal viability of the primary neurons was significantly decreased, thereby a NMDA toxicity cell model was established. The effect of culturing with CsA and GCAP for 3 h on restoring cell viability was examined with cytotoxicity rating assay CCK-8. After treating with CsA or GCAP at 37° C. for 3 h, 10 μl CCK-8 was added and the values were read at 450 nm through a microplate reader.

Figure 3:
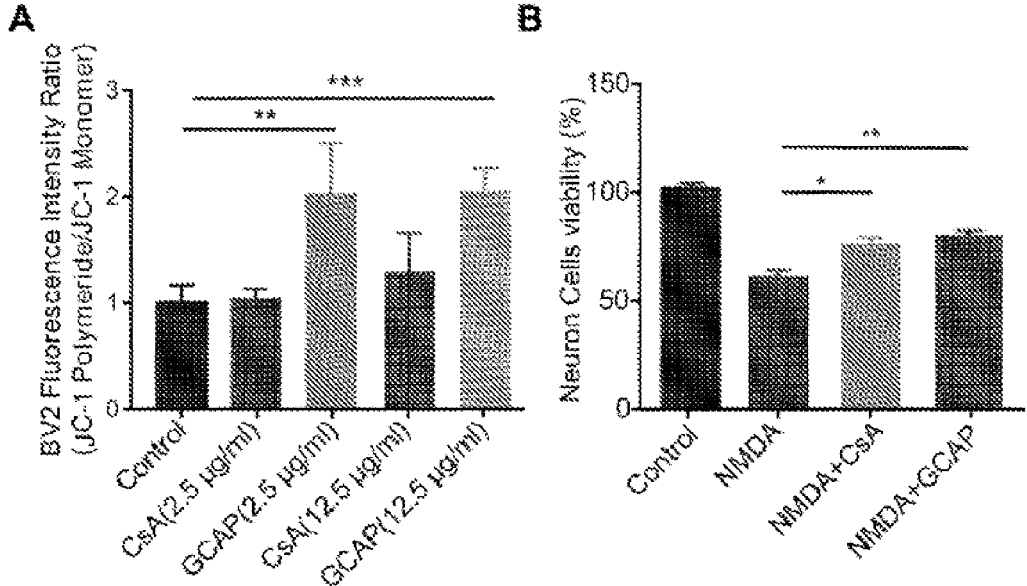
FIG. 3 shows the protection effect of the functional penetrating peptide-modified cyclosporine A-loaded lipid nano drug delivery system (GCAP) on microglia (A) and neurons (B) in vitro, *p<0.05, p<0.01, *p<0.0001.

As shown in FIG. 3, GCAP at low concentrations significantly stabilized the potential level of mitochondrial membrane, and effectively restored the cell viability of injured neurons. The results indicate that the functional penetrating peptide-modified cyclosporine A-loaded lipid nano drug delivery system has a protection effect on microglia and neurons.

Example 4. Targeting Efficiency of the Functional Penetrating Peptide-Modified Lipid Nano Drug Delivery System (GNCP) on Brain Injury Lesion In Vivo (1) Preparation The fluorescence probe DiR loaded functional penetrating peptide (SEQ ID NO: 1)-modified lipid nano drug delivery system was prepared through the same way as described in Example 2.

(2) Establishment of controlled cortical impact model (CCI) in mice: 1) Mice were anesthetized through intraperitoneal injection (5% chloral hydrate, 0.1 mL/10 g), then the heads were fixed on the brain stereotaxic apparatus to expose the anterior fontanel and the right parietal bone, and a bone hole with a diameter of about 4 mm was drilled with bone drill behind 1 mm of the point of anterior fontanel, on the right side of the sagittal suture, followed by removing the bone flap to expose the intact dura mater. 2) Brain of the mice was impacted with a CCI brain stereotaxic impactor, wherein the parameters were set as follows: the diameter of the impact head was 3 mm, the impact speed was 3 m/s, the impact depth was 1 mm, and the retention time was 85 ms. 3) The manipulator arm on the brain stereotaxic impactor was adjusted appropriately; the impact was complete by clicking the impact button when the impact head and the surface of mater fit closely with an alarm sound. 4) The scalp was sutured immediately subsequent to the completion of the impact, and the mice were placed in the animal intensive care unit at 37° C. for recovery. The same anesthesia and surgical procedures were used in the Sham control, except for the impact procedure.

Observation of the distribution of GNCP in vivo with live imaging in small animals: 8 C57BL/6 male healthy mice were divided into drug administration group and the Sham control according to the random number table, and the fluorescence probe DiR labeled functional penetrating peptide-modified lipid nano drug delivery system was injected into the tail vein on the 7th day after CCI, respectively. The dosing regimen was as follows: the CCI model animals were given with GNCP and GNC at a dosage of DMPC 5 mg/kg, the Sham control was given with GNCP at the same dosage. The mice in each group were euthanized via anesthesia 3 h after the drug administration, followed by isolating the heart, liver, spleen, lung, kidney and intact brain tissues. After rinsing with saline, the organs were placed on a small animal live imager and the images were collected.

Observation of the distribution of the functional penetrating peptide-modified lipid nano drug delivery system in the brain tissue with frozen section: C57BL/6 male healthy mice were divided into the drug administration group and the Sham control randomly, and the fluorescence labeled GNCP carrier was injected into the tail vein on the 7th day after CCI, respectively. The dosing regimen was the same as described above. The mice were euthanized 3 h via anesthesia after the drug administration, and the intact brains were isolated and fixed in 4% paraformaldehyde at 4° C. for 24 h. Then the fixed brain tissues were sequentially placed in 15% sucrose-PBS and 30% sucrose-PBS for gradient dehydration to subsidence, and the dehydrated brain tissues were embedded with optimal cutting temperature solution (O.C.T) and solidified at −20° C. After the solidification, the brain tissue was subjected to serial coronal section (20 μm) with frozen slicer. Then the sections were dried at room temperature. After rinsing in PBS, the sections were incubated with 100 ng/mL DAPI for staining the nuclear in the dark for 30 min, followed by rinsing again in PBS. After wiping off the water, the sections were sealed with sealing solution and stored in the dark. The images of the sections were collected using a laser confocal microscope with laser wavelengths of 405 nm and 568 nm.

Figure 4:
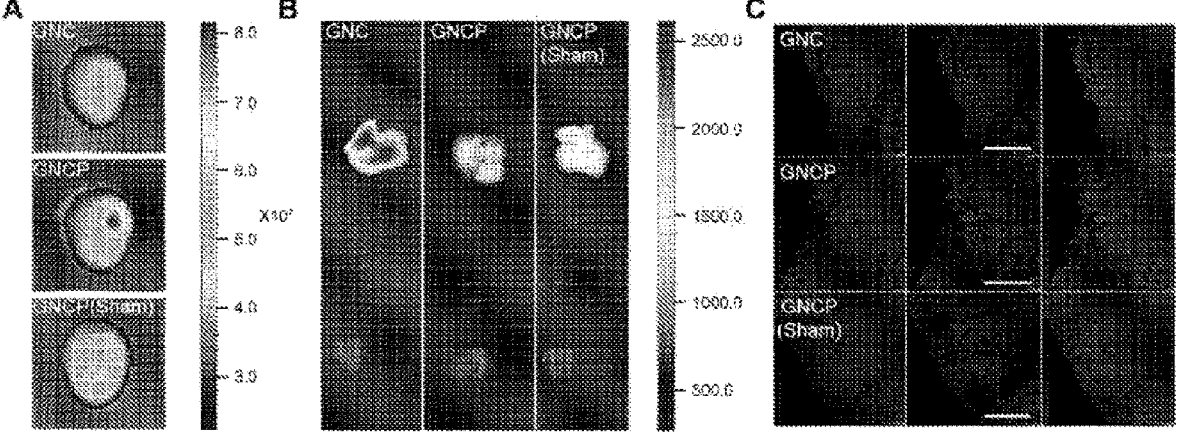
FIG. 4 shows the targeting effect of the functional penetrating peptide-modified lipid nano drug delivery system (GNCP) on brain injury lesion in vivo, scale bars: 400 μm and 500 mm.
Figure 4:
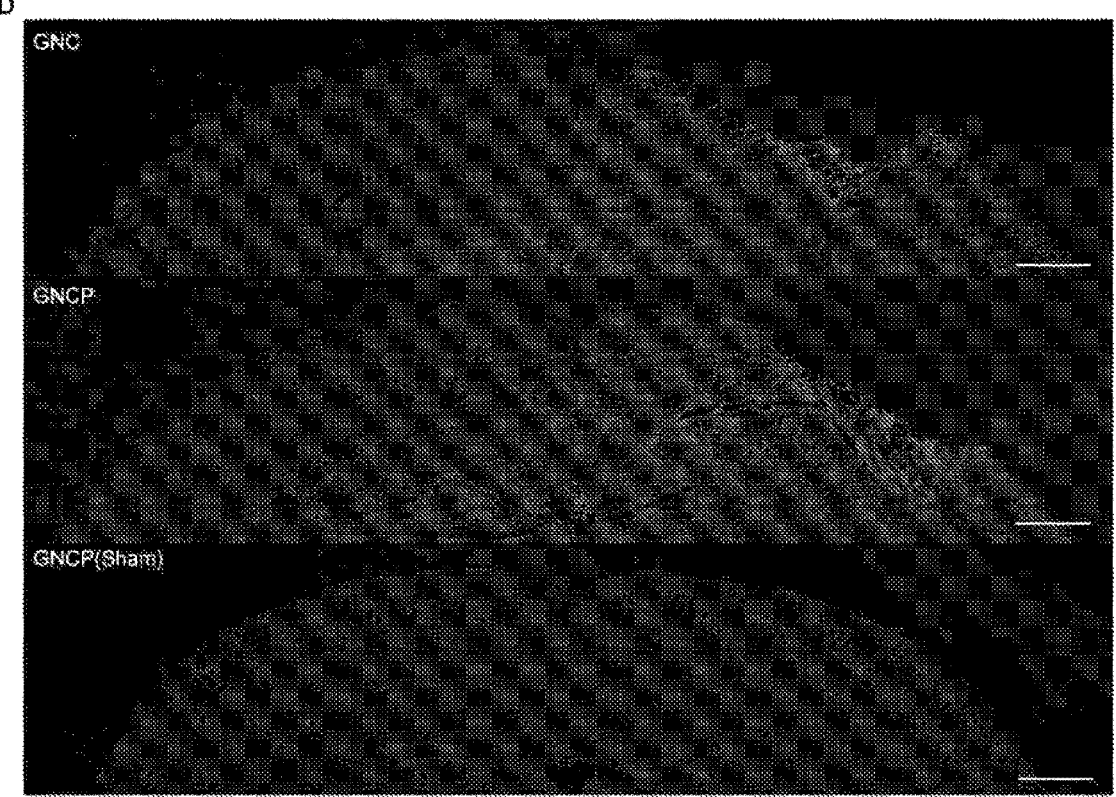

As shown in FIG. 4, at the brain injury site, the distribution of GNCP that contained the functional penetrating peptide is higher than that of GCP that without the functional penetrating peptide (A), and less distributed in the surrounding major organs (B). The fluorescence level of GNCP in the brain parenchyma at the injury side is significantly higher than that of GNC, indicating that more GNCP nanocarrier aggregated at the injury site (C). The images of whole brain section further confirm the aggregation of GNCP in brain injury lesion (D).

Example 5. The Pharmacodynamic Evaluation of the Functional Penetrating Peptide-Modified Cyclosporine A-Loaded Lipid Nano Drug Delivery System (GCAP) Against Brain Injury In Vivo (1) Preparation The preparation method of GCAP is the same as described in Example 1, wherein the functional penetrating peptide is SEQ ID NO: 1.

(2) The CCI model C57BL/6 mice of the Sham control were given saline; injury model group (CCI) was given saline; CsA solution group was given 20 mg/kg/d of CsA; GNCP group was given GNCP solution with a lipid concentration of 16 mg/kg/d; GCAP group was given GCAP solution with a lipid concentration of 16 mg/kg/d (corresponding to CsA concentration of 1.26 mg/kg/d). Each group has three mice which were administrated with the drugs continuously for 7 days. Then the mice were euthanized via anesthesia and fixed with 4% paraformaldehyde solution after perfusion with 0.9% saline. The intact brain was isolated and fixed at 4° C. in 4% paraformaldehyde solution overnight, followed by waxing and paraffin embedding. Finally, the brains were sectioned with a thickness of 5 μm.

Immunohistochemical staining with antibody to glial fibrillary acidic protein (GFAP) revealed the activation of astrocytes in the brain of CCI model mice after drug administration, and the sections were observed and photographed under a microscope.

The pathological changes of neurons in the brain of CCI model mice after drug administration were detected with Nissl staining. Paraffin sections were dewaxed and Nissl stained with toluidine blue staining solution for 3 min After the staining, the sections were differentiated with 95% alcohol and finally dried with a baking machine, and sealed by neutral resin. The sections were observed and photographed under a microscope.

Immunohistochemical staining with antibody to microglia-specific antibody (IBA1) revealed the activation of microglia in the brain of the mice after drug administration, and the sections were observed and photographed under a microscope.

Figure 5:
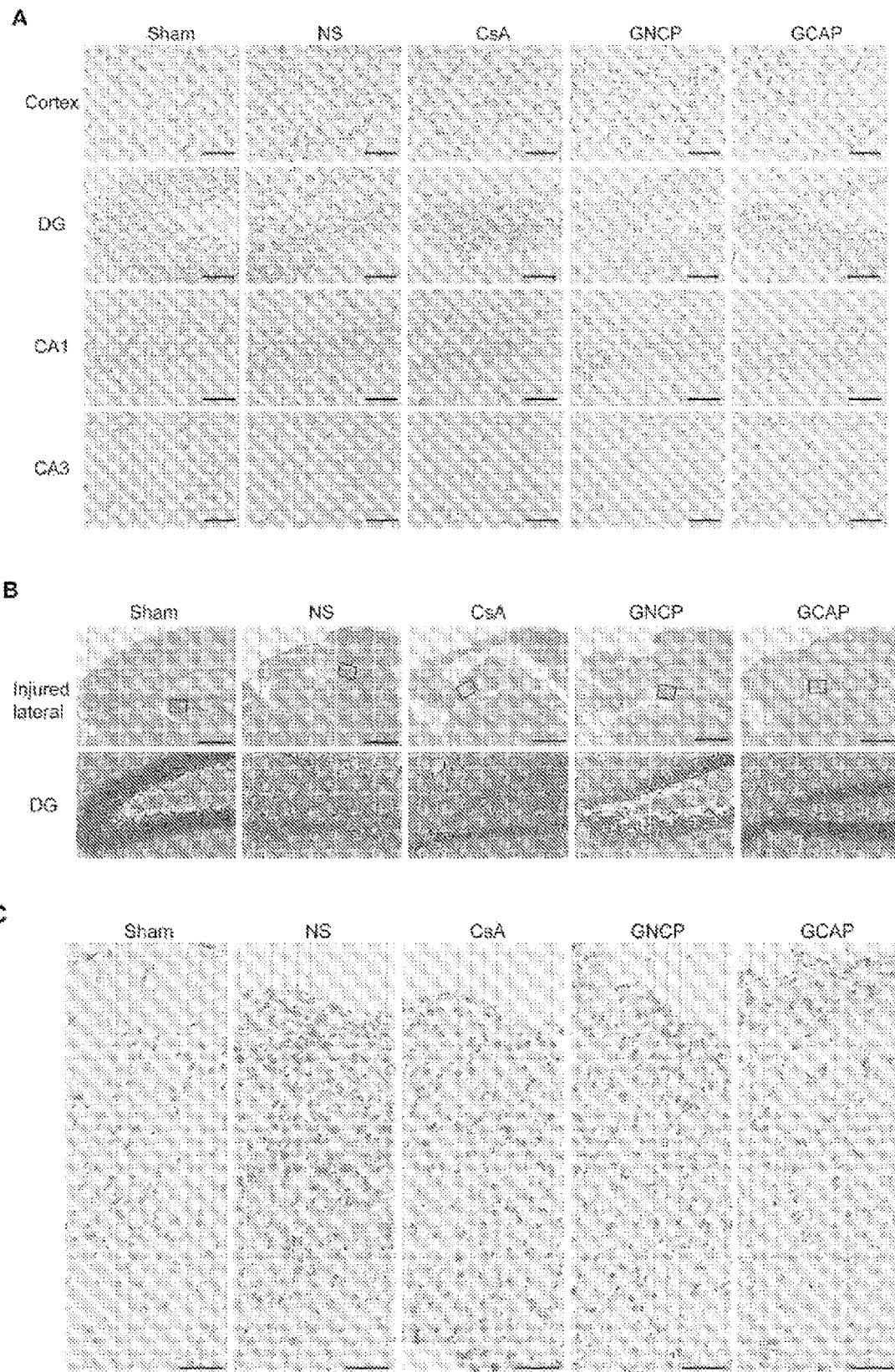
FIG. 5 shows the pharmacodynamic evaluation of the functional penetrating peptide-modified cyclosporine A-loaded lipid nano drug delivery system (GCAP) against brain injury in vivo, scale bar: 500 μm.

As shown in FIG. 5, GCAP effectively reduces the activation of GFAP-labeled astrocytes (A) and IBA1-labeled microglia (C), and also has a significant therapeutic effect on the pathological changes of neurons. The pathological lesion of neurons on the injured side of the brain are significantly improved compared to the saline group, while the morphology of normal hippocampal as well as cortical neurons in the contralateral side of the mice maintains. However, after the administration of the CsA solution for a week, the cell arrangement was still scattered and the tissue edema was obvious, suggesting that CsA exerts no obvious inhibitory and repairing effect on the pathological changes of neurons (B). In contrast, GCAP at the dose of 1.26 mg/kg/d, which is only one sixteenth of that of the CsA solution, achieved better curative effect.

Example 6. Evaluation of Improvement of Cognitive Function in Mice Following the Treatment of the Functional Penetrating Peptide-Modified Cyclosporine A-Loaded Lipid Nano Drug Delivery System (GCAP)

(1) Preparation

The preparation method of GCAP is the same as described in Example 1, wherein the functional penetrating peptide is SEQ ID NO: 1.

(2) The CCI model C57BL/6 mice were randomly grouped into 6 mice per group and administered through tail intravenous injections for 14 d as follows: the Sham control was given with saline; injury model group (CCI) was given with saline; CsA solution group was given with 20 mg/kg/d of CsA; GNCP group was given GNCP solution at the lipid concentration of 16 mg/kg/d; GCAP group was given GCAP solution at the lipid concentration of 16 mg/kg/d (corresponding to CsA concentration of 1.26 mg/kg/d).

Morris Water Maze Test:

Mice of each group were subjected to behavioral training and testing using Morris water maze after 14 days of the administration. The water maze consisted of a circular pool, a platform and a recording system. The circular pool was 150 cm in diameter and 50 cm in height which was divided into four quadrants: I, II, III and IV. The pool was filled with water for 30 cm deep, and white edible titanium dioxide was added to make the water opaque, and the water temperature was kept at about 25° C. The pool was surrounded by spatial references and the positions thereof were kept constant (doors, cameras and wall signs, etc.) for the mice to locate and learn to remember the location of the platform. The cylindrical transparent platform was 9 cm in diameter and 28 cm in height, wrapped in white cloth and placed in quadrant IV, with the surface 2 cm below the water surface. A camera was placed in the center of the pool, and a Morris Water Maze Video Analysis System 2.0 was used to monitor and record the mice's swimming trajectory. During the behavioral test, the room was kept quiet, the light was soft and consistent, and the position of each reference object was kept constant.

Positioning navigation test: this test started from the $9^{th}$ day of the continuous administration and last for 5 days. In daily training, the mice were released into the water facing the pool wall from the water entry points in quadrants I, II, III and IV according to the principle of random arrangement. The order of water entry every two consecutive days was different, the computerized video analysis system monitored and recorded the mice's swimming trajectory and the time required to find the platform from the entry point in real time (escape latency). Each mouse was trained four times a day, and the escape latency was set at 90 s. If the mouse did not find the platform within 90 s, it was guided to the platform and kept there for 30 s. The latency period was then recorded as 90 s.

Spatial probe test: after 5 days of positioning navigation test, the platform was removed on the $6^{th}$ day, and the mice were released into the water facing the pool wall from the water entry points in quadrants I and III respectively, and the percentage of time the mice spent in the quadrant where the platform was located within 60 s as well as the trajectory of the mice searching for the platform and the number of times they crossed the platform were recorded.

Figures 6, 7:
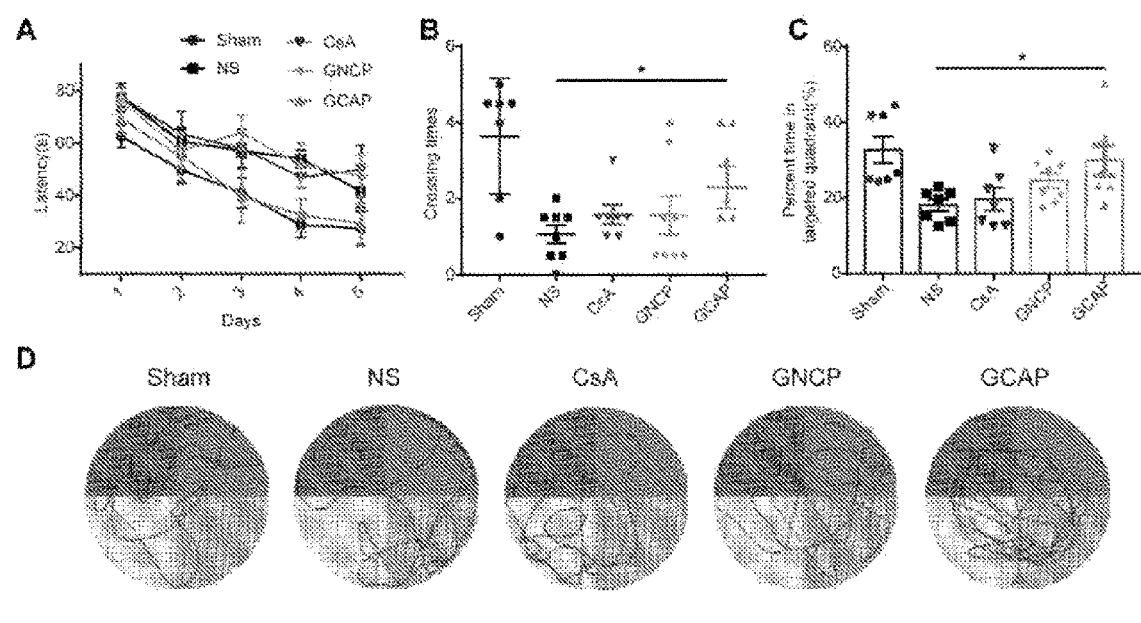
FIG. 6 shows the evaluation of the improvement of cognitive function in mice treated with the functional penetrating peptide-modified cyclosporine A-loaded lipid nano drug delivery system (GCAP), *p<0.05.
FIG. 7 shows the safety evaluation of the functional penetrating peptide-modified cyclosporine A-loaded lipid nano drug delivery system (GCAP). scale bar: 100 μm.

As shown in FIG. 6, the results of the position navigation test showed that from the $2^{nd}$ day the Sham control and GCAP-treated mice found the platform faster than the other four groups (A). And the number of crossing the platform (B), the percentage of time staying in the target platform quadrant (C) and the swimming trajectory (D) of the mice in the spatial probe test showed that the exploration paths of the mice in the Sham control and GCAP group were closer to the platform position. The results indicating that GCAP has a significant improvement on spatial learning memory ability in the brain injury model CCI mice.

Example 7. Evaluation of the Safety of the Functional Penetrating Peptide-Modified Cyclosporine A-Loaded Lipid Nano Drug Delivery System (GCAP)

(1) Preparation

The preparation method of GCAP is the same as described in Example 1, wherein the functional penetrating peptide is SEQ ID NO: 1.

(2) After the Morris water maze test, the heart, liver, spleen, lung as well as kidney of mice were isolated, then prepared into wax blocks and sectioned. The sections of the tissues and organs were stained with HE, observed under a microscope and photographed to preliminarily evaluate the safety of GCAP in vivo.

As shown in FIG. 7, in the liver and spleen tissues where the nanocarriers are easily aggregated, the hepatocytes are not turbid and swollen, there is no intralobular inflammation, and the splenic white and red marrow structures are clear and show no visible morphological changes under a microscope; in the heart and lung tissues where the distribution is less, the myocardial fibers show no abnormalities, and the alveolar structures in the lung tissues are normal. In the kidney tissues, the glomeruli and tubules are normal in structure and show no visible morphological changes under a microscope. The results show that there is no significant damage in the major peripheral tissues and organs of CCI model mice after 14 days of continuous tail vein administration of GCAP.

Example 8. The Microfluidic Preparation Methods

Two-step method: 7.2 mg of DMPC and 0.5 mg of cyclosporin A were dissolved with 1 ml of anhydrous ethanol to prepare the alcohol phase, while 7 ml of ultrapure water was used as the aqueous phase. The alcohol phase and aqueous phase passed through the microfluidic chip at a volume ratio of ethanol:water of 1:7 to prepare a cyclosporine A-loaded lipid nano solution. The obtained lipid nano solution was then added with the penetrating peptide aqueous solution and assembled into cyclosporine A-loaded MMP-sensitive lipid nano drug delivery system (Formulation 1) by passing through the microfluidic system at a volume ratio of 1:1. Finally, the ethanol in the solvent of the prepared Formulation 1 was removed using an ultra-filtration centrifugal tube with a retained molecular weight of 10 kDa, then the lipid nano drug delivery system was suspended to 2 ml with ultrapure water. The light scattering particle size and zeta potential were measured with Zeta-sizer.

One-step method: 7.2 mg of DMPC and 0.5 mg of cyclosporin A were dissolved with 1 ml of anhydrous ethanol to prepare the alcohol phase. Then 40 µl 1 mg/ml aqueous solution of the penetrating peptide was dissolved in 6960 µl ultrapure water to prepare aqueous phase with total volume of 7 ml. The alcohol phase and aqueous phase passed through the microfluidic chip with a volume ratio of ethanol:water of 1:7 to prepare the cyclosporine A-loaded MMP-sensitive lipid nano drug delivery system (Formulation 2). Finally, the ethanol in the solvent of the prepared Formulation 1 was removed using an ultrafiltration centrifugal tube with a retained molecular weight of 10 kDa, then the lipid nano drug delivery system was suspended to 2 ml with ultrapure water. The light scattering particle size and zeta potential were measured with Zetasizer.

The results showed that the particle sizes of Formulation 1 and Formulation 2 are 28.03±2.35 nm and 29.69±1.92 nm, respectively, and the polydiseperse index (PDI) are 0.13 and 0.23, respectively, and the zeta potentials are −8.26±0.27 and −1.36±0.74 mV, respectively, indicating that the particle sizes and their distributions of the resulting formulations are not significantly affected by either the two-step or one-step microfluidic preparation methods.

Example 9. Optimization of the Functional Penetrating Peptide

The functional peptide was synthesized through solid phase peptide synthesis method. The specific method for the preparation of the peptides: the corresponding amino acids were conjugated to a chloromethyl polystyrene resin, and the amino protection group was removed under the protection of trifluoroacetic acid. The peptide conjugated to the resin was then hydrolyzed with hydrogen fluoride, then precipitated in ether ice bath. After dissolving the precipitate in acetonitrile, the solution was subjected to rotary evaporation. The peptide was further purified in an acetonitrile-water system.

The cyclosporine A-loaded lipid nano drug delivery system with a ratio of the penetrating peptide to lipid of 1:100 was prepared through the same one-step method as described in Example 8 (as in Table 1), red fluorescent probe DiI (accounting for 1% of the lipid mass) was added at the time of lipid film formation. The functional peptides were α-helix penetrating peptides with terminal acetylation:

```
                                        (SEQ ID NO: 1)
Ac-FAEKFKEAVKDYFAKFWD-GSG-RRRRRRRRR-PVGLIG-
EGGEGGEGG,
```

```
                                        (SEQ ID NO: 2)
Ac-FAEKFKEAVKDYFAKFWD-GAGA-RRRRRRRRR-PVGLIG-
EGGEGGEGG,
```

```
                                        (SEQ ID NO: 3)
Ac-FAEKFKEAVKDYFAKFWD-GG-RRRRRRRRR-PVGLIG-
EGGEGGEGG,
```

```
                                        (SEQ ID NO: 4)
Ac-FAEKFKEAVKDYFAKFWD-GSG-RRRRRRRRRRRRRRRRR-
PVGLIG-EGGEGGEGG,
```

```
                                        (SEQ ID NO: 5)
Ac-FAEKFKEAVKDYFAKFWD-GSG-RRRRRRRRR-PVGLIG-
EEEEEDDDDK,
```

```
                                        (SEQ ID NO: 6)
Ac-FAEKFKEAVKDYFAKFWD-GSG-RRRRRRRRR-PVGLIG-
EDDDDK,
```

```
                                        (SEQ ID NO: 7)
Ac-FAEKFKEAVKDYFAKFWD-GS G-RRRRRRRRR-
GGGERGPPGPQGAARGFZGTPGL-EGGEGGEGG,
```

```
                                        (SEQ ID NO: 8)
Ac-FAEKFKEAVKD YFAKFWD-GSG-RRRRRRRRR-GPLGLLGC-
EGGEGGEGG
and
```

```
                                        (SEQ ID NO: 9)
Ac-FAEKFKEAVKDYFAKFWD-GSG,
```

```
                                        (SEQ ID NO: 10)
Ac-FAEKFKEAVKDYFAKFWD-GAGA,
```

```
                                        (SEQ ID NO: 11)
Ac-FAEKFKEAVKDYFAKFWD-GG,
```

```
                                        (SEQ ID NO: 12)
RRRRRRRRR,
```

```
                                        (SEQ ID NO: 13)
RRRRRRRRRRRRRRRRR,
```

```
                                        (SEQ ID NO: 14)
PVGLIG,
```

```
                                        (SEQ ID NO: 15)
GGGERGPPGPQGAARGFZGTPGL,
```

```
                                        (SEQ ID NO: 16)
GPLGLLGC,
```

```
                                        (SEQ ID NO: 17)
EGGEGGEGG,
```

```
                                        (SEQ ID NO: 18)
EDDDDK,
```

```
                                        (SEQ ID NO: 19)
EEEEEDDDDK,
```

```
                                        (SEQ ID NO: 20)
Ac-FAEKFKEAVKDYFAKFWD-GSG-RRRRRRRRR-
GERGPPGPQGAARGFZGTPGL-EGGEGGEGG,
```

```
                                        (SEQ ID NO: 21)
Ac-FAEKFKEAVKDYFAKFWD-GSG-RRRRRRRRR,
```

```
                                        (SEQ ID NO: 22)
Ac-FAEKFKEAVKDYFAKFWD-GAGA-RRRRRRRRRRRRRRRRR
and
```

```
                                        (SEQ ID NO: 23)
Ac-FAEKFKEAVKDYFAKFWD-GG-RRRRRRRRRRRRRRRRR-
PVGLIG.
```

The particle size and the surface potential were determined with a laser particle size measurement. The primary astrocytes were cultured in 96-well plates, and the above lipid nano drug delivery systems containing different penetrating peptides were added to the plate in the presence of MMP-9 (500 ng·mL$^{-1}$). After incubating at 37° C. for 3 h, the astrocytes were fixed in 3.7% formaldehyde for 10 minutes, and then the nuclear was stained with DAPI. The uptake of each preparation into the cells was analyzed through a high-definition drug analysis system. The results showed that the levels of the cellular uptake of the lipid nano drug delivery systems containing the functional penetrating peptides (sequences shown in SEQ ID NO: 1, SEQ ID NO: 2, SEQ ID NO: 3, SEQ ID NO: 4, SEQ ID NO: 5, SEQ ID NO: 6, SEQ ID NO: 7 and SEQ ID NO: 8) were all significantly higher than that of the unmodified functional penetrating peptide formulations.

TABLE 1

Characterization of the lipid nano drug delivery systems containing different functional peptides and quantitative data on uptake by primary astrocytes

| | Sequence of functional peptides | Lipid composition | Size (nm) | PDI | Zeta(mV) | The average optical density of nanoparticles containing different functional peptides ingested by cells |
|---|---|---|---|---|---|---|
| Formulation 1 | SEQ ID NO: 1 | DMPC + GMl | 26.50 ± 7.68 | 0.23 | −36.18 ± 3.41 | 143.7 ± 5.20*** |
| Formulation 2 | SEQ ID NO: 2 | DMPC + GMl | 22.23 ± 6.53 | 0.27 | −36.15 ± 1.08 | 100.45 ± 10.53*** |
| Formulation 3 | SEQ ID NO: 3 | DMPC + DSPE | 22.13 ± 5.56 | 0.21 | −36.70 ± 2.12 | 122.47 ± 16.39*** |
| Formulation 4 | SEQ ID NO: 4 | DMPC + GMl | 24.23 ± 5.86 | 0.25 | −30.15 ± 1.40 | 122.47 ± 17 49*** |
| Formulation 5 | SEQ ID NO: 5 | DMPC + GMl | 22.50 ± 8.62 | 0.27 | −36.40 ± 2.10 | 109.46 ± 16.82*** |
| Formulation 6 | SEQ ID NO: 6 | DMPC + GMl | 22.43 ± 9.56 | 0.25 | −37.41 ± 3.14 | 114.54 ± 12.78*** |
| Formulation 7 | SEQ ID NO: 7 | DMPC + GMl | 21.02 ± 4.59 | 0.23 | −37.45 ± 1.04 | 118.71 ± 11.94*** |
| Formulation 8 | SEQ ID NO: 8 | DSPG | 28.59 ± 5.82 | 0.19 | −36.97 ± 5.01 | 99.47 ± 77.49*** |
| Formulation 9 | SEQ ID NO: 9 | DMPC + GMl | 20.41 ± 6.29 | 0.31 | −39.23 ± 5.26 | 42.41 ± 11.92 |
| Formulation 10 | SEQ ID NO: 10 | DMPC + GMl | 29.45 ± 7.89 | 0.23 | −42.13 ± 5.14 | 45.97 ± 18.52 |
| Formulation 11 | SEQ ID NO: 11 | DMPC + GMl | 29.61 ± 4.34 | 0.28 | −41.22 ± 3.56 | 39.84 ± 14.57 |
| Formulation 12 | SEQ ID NO: 12 | DMPC + GMl | 350.25 ± 24.53 | 0.87 | Double peaks appear and cannot be measured accurately | Not detected |
| Formulation 13 | SEQ ID NO: 13 | DMPC + GMl | 250.14 ± 14.89 | 0.77 | Double peaks appear and cannot be measured accurately | Not detected |
| Formulation 14 | SEQ ID NO: 14 | DMPC + GMl | 158.62 ± 21.34 | 0.65 | Double peaks appear and cannot be measured accurately | Not detected |
| Formulation 15 | SEQ ID NO: 15 | DMPC + GMl | 262.46 ± 14.73 | 0.73 | Double peaks appear and cannot be measured accurately | Not detected |
| Formulation 16 | SEQ ID NO: 16 | DMPC + GMl | 169.43 ± 14.69 | 0.80 | Double peaks appear and cannot be measured accurately | Not detected |
| Formulation 17 | SEQ ID NO: 17 | DMPC + GMl | 145.23 ± 23.56 | 0.71 | Double peaks appear and cannot be measured accurately | Not detected |
| Formulation 18 | SEQ ID NO: 18 | DMPC + GMl | 147.45 ± 17.77 | 0.62 | Double peaks appear and cannot be measured accurately | Not detected |

TABLE 1-continued

Characterization of the lipid nano drug delivery systems containing different
functional peptides and quantitative data on uptake by primary astrocytes

| | Sequence of functional peptides | Lipid composition | Size (nm) | PDI | Zeta(mV) | The average optical density of nanoparticles containing different functional peptides ingested by cells |
|---|---|---|---|---|---|---|
| Formulation 29 | SEQ ID NO: 19 | DMPC + GMl | 162.53 ± 10.28 | 0.56 | Double peaks appear and cannot be measured accurately | Not detected |
| Formulation 20 | SEQ ID NO: 20 | DMPC + GMl | 25.65 ± 3.45 | 0.23 | −32.45 ± 4.52 | 43.56 ± 8.26 |
| Formulation 21 | — | DMPC + GMl | 27.16 ± 4.52 | 0.16 | −22.33 ± 0.46 | 39.45 ± 5.43 |
| Formulation 22 | SEQ ID NO: 1 | DMPC | 26.50 ± 7.68 | 0.23 | −6.16 ± 1.23 | 132.57 ± 9.82*** |
| Formulation 23 | SEQ ID NO: 21 | DMPC + GMl | Unstable, precipitated, not detected | | | Not detected |
| Formulation 24 | SEQ ID NO: 22 | DMPC + GMl | Unstable, precipitated, not detected | | | Not detected |
| Formulation 25 | SEQ ID NO: 23 | DMPC + GMl | Unstable, precipitated, not detected | | | Not detected |

"—"without the functional peptides.
***P < 0.001 significantly different from the group without the functional peptides.

Those described above are only preferred examples of the present invention, and it should be noted that for those of skill in the art, various improvements and modifications can be made without departing from the principles of the present invention, and these improvements and modifications shall also fall within the scope of protection of the present invention.

What is claimed is:

1. A lipid nano drug delivery system targeting brain lesion, wherein the drug delivery system comprises lipids, a delivery drug and a functional penetrating peptide, and the functional penetrating peptide has a sequence of one of the following peptides with terminal acetylation:

```
SEQ ID NO: 1:
Ac-FAEKFKEAVKDYFAKFWD-GSG-RRRRRRRRR-PVGLIG-
EGGEGGEGG,

SEO ID NO: 2:
Ac-FAEKFKEAVKDYFAKFWD-GAGA-RRRRRRRRR-PVGLIG-
EGGEGGEGG,

SEP ID NO: 3:
Ac-FAEKFKEAVKDYFAKFWD-GG-RRRRRRRRR-PVGLIG-
EGGEGGEGG,

SEP ID NO: 4:
Ac-FAEKFKEAVKDYFAKFWD-GSG-RRRRRRRRRRRRRRRRRR-
PVGLIG-EGGEGGEGG,

SEP ID NO: 5:
Ac-FAEKFKEAVKDYFAKFWD-GSG-RRRRRRRRR-PVGLIG-
EEEEEDDDDK,

SEP ID NO: 6:
Ac-FAEKFKEAVKDYFAKFWD-GSG-RRRRRRRRR-PVGLIG
EDDDDK.

SEP ID NO: 7:
Ac-FAEKFKEAVKDYFAKFWD-GSG-RRRRRRRRR-
GGGERGPPGPQGAARGFZGTPGL-EGGEGGEGG,

SEP ID NO: 8:
Ac-FAEKFKEAVKDYFAKFWD-GSG-RRRRRRRRR-GPLGLLGC-
EGGEGGEGG.
```

2. The lipid nano drug delivery system targeting brain lesion of claim 1, wherein the functional penetrating peptide has a mass ratio of 1:10-1:300 to the lipid.

3. The lipid nano drug delivery system targeting brain lesion of claim 1, wherein the delivery drug comprises cyclosporine A, vasoactive peptides, enkephalins, endorphins and neurotensin.

4. The lipid nano drug delivery system targeting brain lesion of claim 3, wherein the delivery drug is cyclosporine A, and the cyclosporine A is prepared by a dilution-induced precipitation.

5. The lipid nano drug delivery system targeting brain lesion of claim 4, wherein the cyclosporine A has a mass ratio of 1:1-1:100 to the lipid.

6. A method for treating brain injury disease, comprising administering effective amount of the lipid nano drug delivery system targeting brain lesion of claim 1 to a patient in need thereof.

7. A functional penetrating peptide for modifying a lipid nano drug delivery system targeting brain lesion, wherein the functional penetrating peptide has a sequence of one of the following peptides with terminal acetylation:

```
SEQ ID NO: 1:
Ac-FAEKFKEAVKDYFAKFWD-GSG-RRRRRRRRR-PVGLIG-
EGGEGGEGG,

SEO ID NO: 2:
Ac-FAEKFKEAVKDYFAKFWD-GAGA-RRRRRRRRR-PVGLIG-
EGGEGGEGG,

SEP ID NO: 3:
Ac-FAEKFKEAVKDYFAKFWD-GG-RRRRRRRRR-PVGLIG-
EGGEGGEGG,

SEP ID NO: 4:
Ac-FAEKFKEAVKDYFAKFWD-GSG-RRRRRRRRRRRRRRRRRR-
PVGLIG-EGGEGGEGG,

SEP ID NO: 5:
Ac-FAEKFKEAVKDYFAKFWD-GSG-RRRRRRRRR-PVGLIG-
EEEEEDDDDK,

SEP ID NO: 6:
Ac-FAEKFKEAVKDYFAKFWD-GSG-RRRRRRRRR-PVGLIG-
EDDDDK.

SEP ID NO: 7:
Ac-FAEKFKEAVKDYFAKFWD-GSG-RRRRRRRRR-
GGGERGPPGPQGAARGFZGTPGL-EGGEGGEGG,

SEP ID NO: 8:
Ac-FAEKFKEAVKDYFAKFWD-GSG-RRRRRRRRR-GPLGLLGC-
EGGEGGEGG.
```

8. A method for preparing a lipid nano drug delivery system targeting brain lesion, which comprises loading the functional penetrating peptide for modifying a lipid nano drug delivery system targeting brain lesion of claim 7.

9. A preparation method of the lipid nano drug delivery system targeting brain lesion of claim 4, wherein the preparation method comprises a stepwise method or a one-step method, wherein the stepwise method comprises following steps:

a) prepare the precipitated solution of cyclosporin A by a dilution-induced precipitation;

b) prepare a cyclosporine A-loaded lipid nano drug delivery system;

c) prepare the cyclosporine A-loaded lipid nano drug delivery system modified with the functional penetrating peptide, by adding the functional penetrating peptide into the lipid nano drug delivery system solution prepared in step b) above;

the one-step method refers to that a cyclosporine A-loaded lipid nano drug delivery system modified with the functional penetrating peptide is directly prepared by self-assembly of lipid, cyclosporine A and the functional penetrating peptide through microfluidic chip.

10. The preparation method of the lipid nano drug delivery system targeting brain lesion of claim 9, wherein the induced precipitation of step a) is implemented by microfluidics, the precipitate is formed by passing an aqueous phase and an alcohol phase containing cyclosporine A through microfluidic chip pipeline.

11. The preparation method of the lipid nano drug delivery system targeting brain lesion of claim 9, wherein the cyclosporine A-loaded lipid nano drug delivery system of step b) is prepared by a continuous flow technique of microfluidics, and the cyclosporine A-loaded lipid nano drug delivery system is obtained by self-assembly of the cyclosporine A and a lipid-containing phase through microfluidic pipeline, wherein the cyclosporine A is prepared by the microfluidic induced precipitation.

12. The lipid nano drug delivery system targeting brain lesion of claim 2, wherein the functional penetrating peptide has a mass ratio of 1:100 to the lipid.

13. The lipid nano drug delivery system targeting brain lesion of claim 5, wherein the cyclosporine A has a mass ratio of 1:4 to the lipid.

14. The preparation method of the lipid nano drug delivery system targeting brain lesion of claim 10, wherein the alcohol phase has a volume ratio of 1:1-1:100 to the aqueous phase.

15. The preparation method of the lipid nano drug delivery system targeting brain lesion of claim 14, wherein the alcohol phase has a volume ratio of 1:8 to the aqueous phase.

\* \* \* \* \*